United States Patent
Zuloff et al.

(10) Patent No.: US 8,206,231 B2
(45) Date of Patent: Jun. 26, 2012

(54) MOVABLE NOVELTY TEETH AND METHOD THEREOF

(75) Inventors: Steve Zuloff, Los Angeles County, CA (US); Tak On Chan, Hong Kong (CN)

(73) Assignees: Steve Zuloff, Chatsworth, CA (US); HPI Hong Kong Limited, Hong Kong (HK)

( * ) Notice: Subject to any disclaimer, the term of this patent is extended or adjusted under 35 U.S.C. 154(b) by 332 days.

(21) Appl. No.: 12/658,181

(22) Filed: Feb. 4, 2010

(65) Prior Publication Data

US 2011/0189631 A1    Aug. 4, 2011

(51) Int. Cl.
*A63J 5/02* (2006.01)
*A63J 21/00* (2006.01)
(52) U.S. Cl. .................. 472/70; 472/51; 446/27
(58) Field of Classification Search .............. 472/51, 472/54, 70, 81, 137; 446/26–28; 433/218, 433/229
See application file for complete search history.

(56) References Cited

U.S. PATENT DOCUMENTS

| | | | |
|---|---|---|---|
| 4,676,500 A * | 6/1987 | Fricano | 472/70 |
| 5,083,770 A * | 1/1992 | Holland | 472/70 |
| 5,547,381 A | 8/1996 | Nutting | |
| 5,569,036 A | 10/1996 | Goldiner et al. | |
| 5,951,291 A | 9/1999 | Albert et al. | |
| 6,450,814 B1 | 9/2002 | Britton | |
| 2003/0136416 A1 | 7/2003 | White | |

\* cited by examiner

*Primary Examiner* — Kien Nguyen
(74) *Attorney, Agent, or Firm* — Howard C. Miskin, Esq.; Gloria Tsui-Yip, Esq.

(57) ABSTRACT

An improved novelty teeth device for use with a user's teeth movable between a first concealed position and a second visible position. The novelty teeth device has a pair of spaced apart tooth wells for receiving the user's teeth. Between the tooth wells is a central lever element that connects and interacts with two rods, each of which is inserted across each tooth well. The other end of each rod is connected to a curve arm. At the distal end of each curve arm is one or more teeth elements. When the central lever element is pivoted up or down, it rotates the rods, which causes the curve arms to move up or down, concealing or revealing the teeth elements, respectively. A moldable putty can be used in the tooth well to improve comfort to the user.

25 Claims, 2 Drawing Sheets

MOVABLE NOVELTY TEETH AND METHOD THEREOF

FIELD OF THE INVENTION

The invention relates to movable novelty fangs or teeth and an improved method for securing such novelty teeth or fangs to the wearer's teeth.

BACKGROUND

Halloween is a widely celebrated holiday in the United States and throughout the world. Many cities hold parades, special events, and contests in observance of Halloween. In celebration of Halloween or at costume parties, many individuals choose to dress as vampires or animals with fangs. The use of novelty teeth or fangs also extends beyond Halloween, and includes uses in theatrical productions, movies, games, or personal style. The traditional novelty fangs available are stationary and are sold either as individual fangs to be applied to individual teeth using adhesives, or are part of a complete set of fake teeth, worn over the wearer's natural dentition, and held in place either by biting down on the set of fake teeth, by suction onto the wearer's teeth, or by adhesives.

The traditional novelty fangs or teeth and methods of displaying such fangs or teeth result in the wearer displaying the fangs or teeth at all times while they are attached or held in place. The traditional methods of attaching fangs or teeth result in discomfort to the wearer even for a short period of time, and may result in embarrassment when the improperly positioned fangs fall out of the wearer's mouth. Since the traditional novelty teeth or fangs are mass produced, the fit is not personalized, and the lack of proper fit results in a loose and ill-fitting set of novelty teeth or fangs.

Some prior art novelty teeth tried to improve the comfort to a wearer with the use of a layer of curable polymer. Such prior art curable polymer requires the wearer to prepare, mix, homogenize and cure the material prior to use. Further, such curable polymer often involves the use of chemical having unpleasant odor.

Therefore, there is a need for an improved novelty teeth or fangs that is comfortable to the wearer and provides more entertaining value.

SUMMARY OF THE INVENTION

The improved novelty teeth or fangs and the method of the present invention allows a wearer to comfortably wear the novelty teeth or fangs in the wearer's mouth. The present invention also provides the wearer of the novelty teeth or fangs with the ability to selectively conceal or reveal the teeth or fangs without having to remove the device from the wearer's mouth.

The present invention is a novelty teeth or fangs device movable between a first concealed position and a second visible position for use with a user's teeth. The novelty teeth or fangs includes a pair of spaced apart tooth wells, each tooth well having a base with a through opening extending across the base, wherein each tooth well is adapted to partially surround some of the user's teeth; a pair of rods, each rod rotatably positioned in each opening having first and second ends wherein the pair of rods has a common axis; a central lever element between the pair of tooth wells and attached to said first ends of each rod, wherein said central lever element is pivotable around said common axis; a pair of curve arms, each curve arm extending from the second ends of each rod, wherein the curve arms are adapted to substantially conform to the curvature of the user's upper teeth; and one or more teeth elements, such as fangs or teeth, at the distal end of each curve arm. The pivotal movement of the central lever element translates to rotational movement of the rods, which translate to pivotal movement of the teeth elements via the curve arms, causing the teeth elements to move between the first position and the second position.

The present invention allows the wearer to selectively conceal the novelty teeth or fangs between the upper gums and the upper lip of the wearer. The wearer can then use his or her tongue to push down on the lever positioned inside the wearer's mouth behind the upper teeth, resulting in controlled lowering of the fangs or teeth, thereby giving the appearance that the fangs or teeth are growing, or have suddenly appeared.

The present invention further resolves the problem of fit, comfort and durability of wear associated with the traditional novelty teeth or fangs and methods of application of novelty teeth or fangs, by allowing the wearer to custom-fit the portions of the novelty teeth or fangs which are in contact with the wearer's back teeth. Customization is achieved by using and placing a specialized putty in each tooth well. The specialized putty becomes soft and moldable when placed in hot water. This specialized putty is then molded to the shape of the wearer's teeth when the wearer bites down on the device of the present invention, at the designated position within the wearer's mouth. When cooled the putty hardens to conform to the shape of the wearer's teeth, while still remains pliable to comfortably rest against the wearer's teeth. Once molded, the novelty teeth or fangs allow the wearer to repeatedly and comfortably secure the novelty teeth or fangs in place within the wearer's mouth.

The putty of the present invention does not require prior preparation, mixing, and/or polymerization by the wearer. Further, the putty does not expose the wearer to odors and/or chemical hazards. The moldable putty used in the present invention is easy to handle and prepare, does not release any odor and does not expose the wearer to any chemical hazards.

BRIEF DESCRIPTION OF THE DRAWINGS

Preferred embodiments of the present invention have been chosen for purposes of illustration and description and are shown in the accompanying drawings forming a part of the specification wherein.

DETAILED DESCRIPTION OF THE PREFERRED EMBODIMENTS

Figure 1:
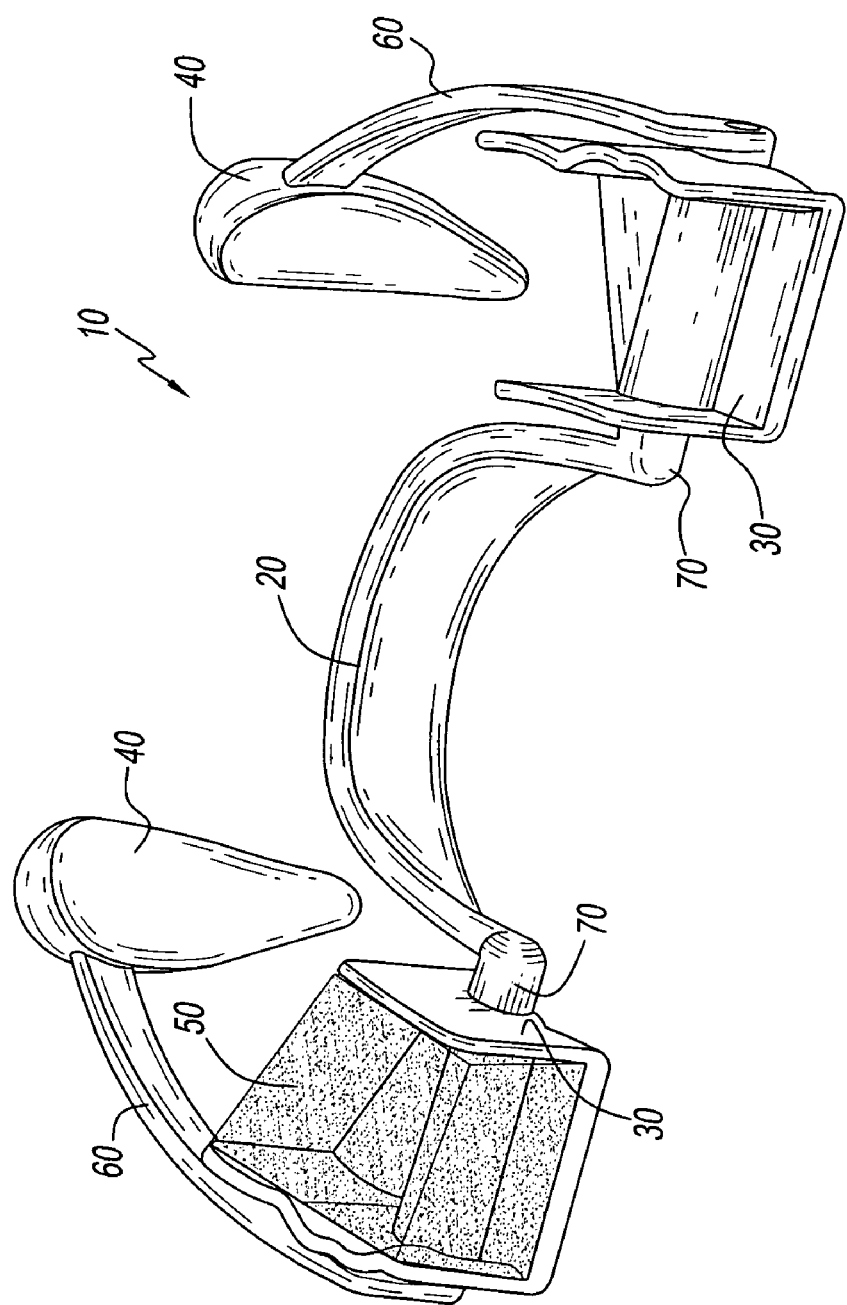
FIG. 1 is a perspective view of the novelty teeth of the present invention.
Figure 2:
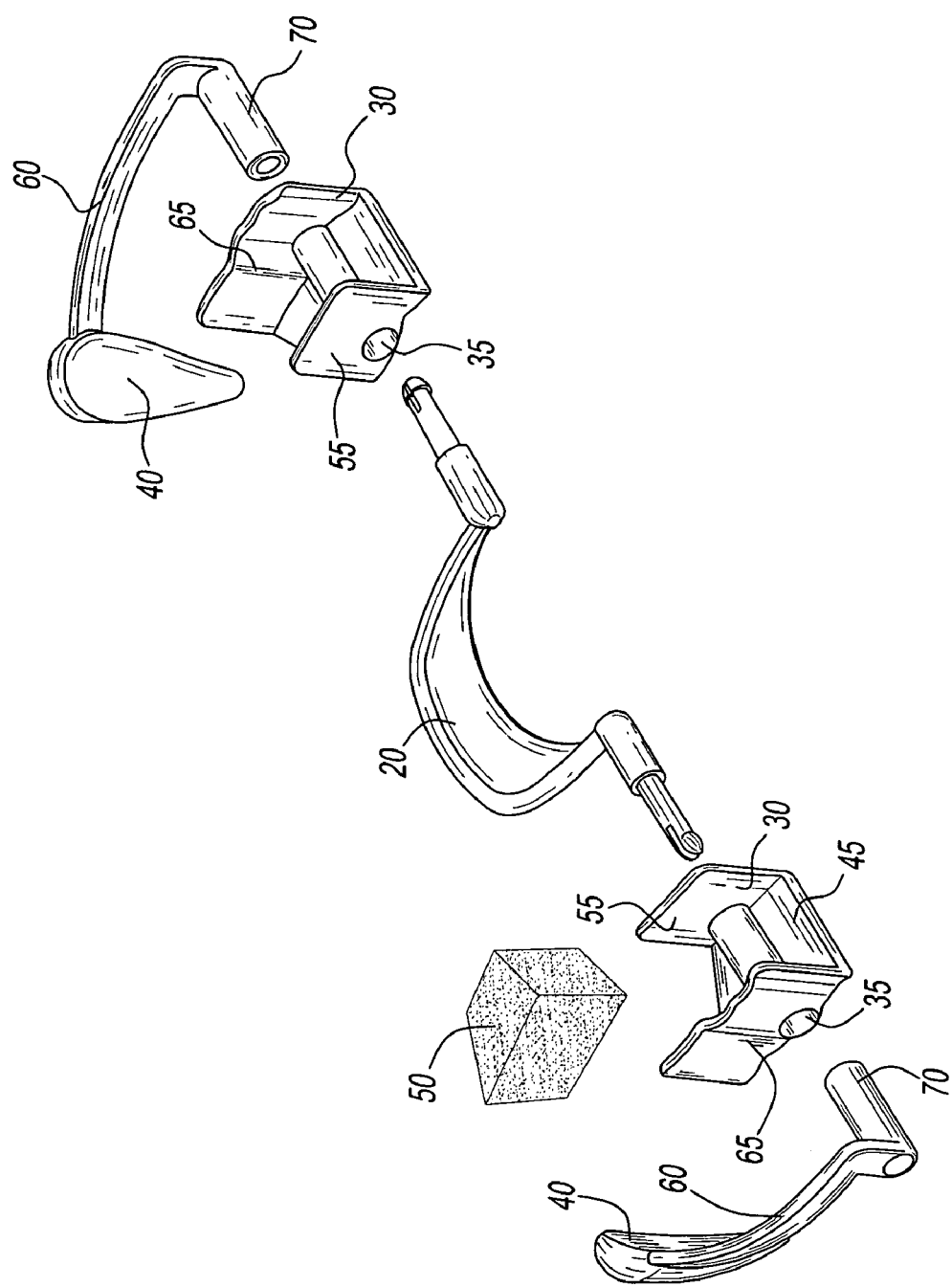
FIG. 2 is an exploded view of FIG. 1.

With reference to the drawings, wherein the same reference number indicates the same element throughout, there is shown in FIGS. 1 and 2 a novelty teeth set 10 of the present invention. Novelty teeth 10 comprises a central lever 20, a pair of tooth wells 30, a pair of rods 70, a pair of teeth elements 40 and a pair of curve arms 60.

As shown in FIGS. 1-2, the central lever element 20 has a crescent (semi-circular) shape for fitting in the wearer's mouth behind the upper teeth, and being manipulatable by the wearer's tongue. The central lever element 20 can also have other shapes known to one skilled in the art for fitting in a wearer's mouth, such as rectangular, triangular, a bar or strap used for lowering or raising said central lever element 20 inside the wearer's mouth. The central lever element 20 can be made of plastic, rubber, silicone, PVC, etc., generally used by one skilled in the art for novelty teeth and mouth pieces. Attached to each end of the central lever element 20 are rods 70.

Each tooth well 30 has a base 45 and a pair of spaced apart opposing walls 55 and 65 extending substantially perpendicular from the base 45. Wall 55 is located at the proximal end of each tooth well 30 in relation to the central lever element 20. Wall 55 has a substantially flat surface. Wall 65 is located at the distal end of each tooth well 30 in relation to the central lever element 20. Wall 65 has a curved or shaped surface to facilitate fit and comfort in the wearer's mouth.

Across each base 45 and extending between the opposing walls 55 and 65 is a thorough opening 35. A rod 70 extends through the opening 35 in each corresponding tooth well 30. The tooth wells 30 move pivotally in relation to the rods 70. The distal end of each rod 70 is connected to a teeth element 40 via a curve arm 60 which are shaped to comfortably fit between the wearer's upper gum and lip. The movement of the central lever element 20 translates into the movement of the teeth elements 40. As shown in FIG. 2, each rod 70 may optionally be formed from extensions integral to the central lever element 20 and the curve arms 60.

Each tooth well 30 is filled with a moldable dental putty 50, which becomes moldable and translucent when heated or warmed. The moldable dental putty 50 in each tooth well 30 can be imprinted with or molded to conform to the wearer's teeth by placing the dental putty 50 in hot water (155° F.-180° F. or 68° C.-82° C.), and then placing it in the wearer's mouth, with the wearer biting down on the dental putty 50. When the dental putty 50 is cured by cooling to room temperature, the dental putty 50 is molded to conform to the wearer's teeth and remains pliable.

With the customized fit of the molded dental putty 50, the wearer can maintain a high level of comfort while wearing the novelty teeth assembly 10. The imprinting of the dental putty 50 allows the tooth wells 30 to form a close fit with the wearer's teeth.

While the teeth elements 40 are shown as fangs, they may also resemble regular teeth or other configurations. Further, the pair of teeth elements 40 may be joined (with no spaces between) to form a row of teeth elements (not shown). To achieve different effect, the teeth elements 40 may be of a natural color, or any other color or have designs, inscriptions, etc., thereon.

When in use, the wearer places the novelty teeth 10 in his/her mouth, with the tooth wells 30 and dental putty 50 wrapping around the upper back teeth or molar teeth. If desired, one tooth well 30, with a corresponding rod 70 and a corresponding curve arm 60 may be used. The central lever 20 is positioned behind the wearer's upper teeth and the curve arms 60 and teeth elements 40 are positioned in front of the wearer's upper teeth and behind the wearer's upper lip, in the first concealed position. To reveal the teeth elements 40 in a second visible position, the wearer uses his/her tongue to push or pivot the central lever element 20 in a downward position. The central element 20 in turn rotates the rods 70, which causes the curve arms 60 and teeth elements 40 to move downward to reveal the teeth elements 40. When the movement of the central lever element 20 is done slowly, the result is dramatic, as if the teeth element 40 grows instantly before one's eyes.

The features of the invention illustrated and described herein are the preferred embodiments. Therefore, it is understood that the appended claims are intended to cover the variations disclosed and unforeseeable embodiments with insubstantial differences that are within the spirit of the claims.

What we claim is:

1. A novelty device movable between a first concealed position and a second visible position for use with a user's teeth, comprising:
   a. a pair of spaced apart tooth wells, each tooth well having a base with a through opening extending across said base, wherein each said tooth well is adapted to partially surround some of the user's teeth;
   b. a pair of rods, each rod rotatably positioned in each said opening having first and second ends, wherein said pair of rods having a common axis;
   c. a central lever element between said pair of tooth wells attached to said first ends of each of said rod, wherein said central lever element is pivotable around said common axis;
   d. a pair of curve arms, each curve arm extending from said second ends of each of said rod, wherein said curve arms are adapted to substantially conform to the curvature of the user's upper teeth; and
   e. one or more teeth elements at the distal end of each of said curve arms;

wherein pivotal movement of said central lever element translates to rotational movement of said rods, which translates to pivotal movement of said teeth elements via said curve arms, causing said teeth elements to move between said first position and said second position.

2. The device of claim 1 wherein said central lever element has a crescent shape.

3. The device of claim 1 wherein each of said tooth wells further having a pair of opposing walls extending substantially perpendicular from said base.

4. The device of claim 3 wherein said wall adjacent said central lever element is substantially flat.

5. The device of claim 3 wherein said wall adjacent said curved arm is curved to conform to the user's teeth.

6. The device of claim 1 wherein each of said teeth elements is fang-shaped.

7. The device of claim 1 wherein a plurality of teeth elements form a continuous row of teeth elements.

8. The device of claim 1, wherein each teeth element is of a natural color.

9. The device of claim 1 further comprising a putty positioned in each tooth well on said base adapted to partially surround some of the user's teeth, wherein said putty is moldable when heated and curable to a malleable form at room temperature.

10. The device of claim 9 wherein said putty is a dental grade putty.

11. The device of claim 9 wherein said putty is moldable when heated to a temperature in the range of approximately 155° F.-180° F.

12. The device of claim 1 wherein each of said rods is formed from corresponding extensions extending from said central lever element and said curve arm.

13. A method for displaying a novelty device for use with a user's teeth movable between a first concealed position and a second visible position, comprising the steps of:
   a. providing a pair of spaced part tooth wells, each tooth well having a base with a through opening extending across said base,
   b. providing a pair of rods, each rod rotatably positioned in each said opening having first and second ends wherein said pair of rods having a common axis;
   c. providing a central lever element between said pair of tooth wells attached to said first ends of each of said rod, wherein said central lever element is pivotable around said common axis;

d. providing a pair of curve arms, each curve arm extending from said second ends of each of said rod, wherein said curve arms are adapted to substantially conform to the curvature of the user's upper teeth;

e. providing one or more teeth elements at the distal end of each of said curve arms;

f. placing said tooth wells in the user's teeth such that said tooth wells partially surround some of the user's upper back teeth, said central lever element is positioned behind the user's upper teeth and said curve arms are positioned between the user's upper gum and upper lip in the first position; and g. pivoting said central lever element with the user's tongue, which translates to pivotal movement of said teeth element via said curve arms, causing said teeth elements to move from said first concealed position to said second visible position.

14. The method of claim 13 wherein said central lever element has a crescent shape.

15. The method of claim 13 wherein each of said tooth wells further having a pair of opposing walls extending substantially perpendicular from said base to partially surround some of the user's upper back teeth.

16. The method of claim 15 wherein said wall adjacent said central lever element is substantially flat.

17. The method of claim 15 wherein said wall adjacent said curved arm is curved to conform to the user's teeth.

18. The method of claim 13 wherein each of said teeth elements is fang-shaped.

19. The method of claim 13 wherein a plurality of teeth elements form a continuous row of teeth elements.

20. The method of claim 13, wherein each teeth element is of a natural color.

21. The method of claim 13 further comprising the steps of:

h. providing a moldable putty to partially surround some of the user's upper back teeth;

i. heating said putty;

j. placing said heated putty in each tooth well;

k. molding said putty to conform to the user's upper back teeth by having the user bite down on the putty in said tooth well to partially surround some of the user's upper back teeth;

l. curing said putty by cooling it to room temperature.

22. The method of claim 21 wherein said moldable putty is a dental grade putty.

23. The method of claim 21 wherein said putty is heated to a temperature in the range of approximately 155° F.-180° F.

24. The method of claim 13 wherein each of said rod is formed from corresponding extensions extending from said central lever element and said curve arm.

25. A novelty device movable between a first concealed position and a second visible position for use with a user's teeth, comprising:

a. at least one tooth well having a base with a through opening extending across said base, wherein said tooth well is adapted to partially surround some of the user's teeth;

b. at least one rod positioned in said opening having first and second ends defining an axis;

c. a central lever element attached to said first end of said rod pivotable around said axis;

d. at least one curve arm extending from said second end of said rod, wherein said curve arm is adapted to substantially conform to the curvature of the user's upper teeth; and e. at least one teeth element at the distal end of said curve arm;

wherein pivotal movement of said central lever element translates to rotational movement of said rod, which translates to pivotal movement of said teeth element via said curve arm, causing said teeth element to move between said first position and said second position.

* * * * *